United States Patent [19]

Frank et al.

[11] Patent Number: 4,569,791
[45] Date of Patent: Feb. 11, 1986

[54] ANTI-DIABETIC COMPOUNDS

[75] Inventors: Bruce H. Frank; Allen H. Pekar, both of Indianapolis, Ind.

[73] Assignee: Eli Lilly and Company, Indianapolis, Ind.

[21] Appl. No.: 620,782

[22] Filed: Jun. 14, 1984

[51] Int. Cl.$^4$ ............................................. C07C 103/52
[52] U.S. Cl. ............................................... 260/112.5 R
[58] Field of Search ................................. 260/112.5 R

[56] References Cited

PUBLICATIONS

Geiger et al., *Chem. Ber.*, 106, 2339-2346, 2347-2352, (1973).
Chemical Abstracts, 82, 49(1975), Abst. No. 68464c.
Chance, Proceedings of the VII Congress of the International Diabetes Federation, Buenos Aires, 1970, Excerpta Medica International Congress Series, No. 231, pp. 292-305.
Kemmler et al., *J. Biol Chem.*, 246, 6787-6791, (1971).
Gutman et al., *Diabetologia* 8, 136-140, (1972).
Chance, *Diabetes* 21, 461-467, (1972).
Yu et al., *J. Biol. Chem.*, 248, 3753-3761, (1973).
Gavin et al., *J. Clin. Endocrinol. Metab.*, 41, 438-445, (1975).
de Haen et al., *J. Clin. Invest.*, 62, 727-737, (1978).

*Primary Examiner*—Delbert R. Phillips
*Assistant Examiner*—F. T. Moezie
*Attorney, Agent, or Firm*—William C. Martens, Jr.; Arthur R. Whale

[57] ABSTRACT

A class of compounds having insulin-like activity is described. These compounds have the formula

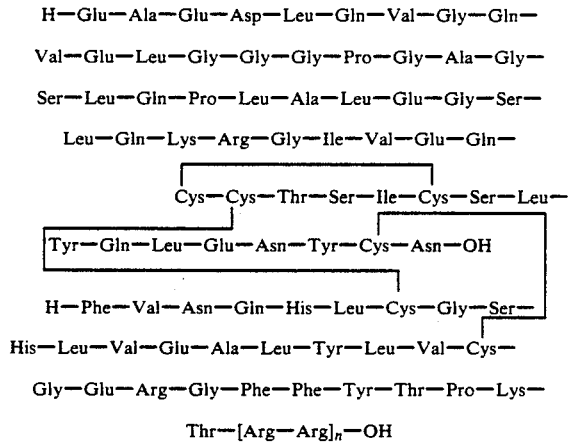

in which n is zero or one.

3 Claims, No Drawings

ANTI-DIABETIC COMPOUNDS

BACKGROUND OF THE INVENTION

This invention is directed to novel compounds having anti-diabetic activity. Each compound of this invention is available by conversion of human proinsulin or an intermediate derived from human proinsulin.

Human proinsulin is recognized to exhibit anti-diabetic activity, albeit at a much lower level, relative to human insulin itself. The compounds of this invention exhibit anti-diabetic activity at a level much greater than that demonstrated by human proinsulin.

SUMMARY OF THE INVENTION

Thus, this invention is directed to a class of compounds having the formula

H—Glu—Ala—Glu—Asp—Leu—Gln—Val—Gly—Gln—

Val—Glu—Leu—Gly—Gly—Gly—Pro—Gly—Ala—Gly—

Ser—Leu—Gln—Pro—Leu—Ala—Leu—Glu—Gly—Ser—

Leu—Gln—Lys—Arg—Gly—Ile—Val—Glu—Gln—

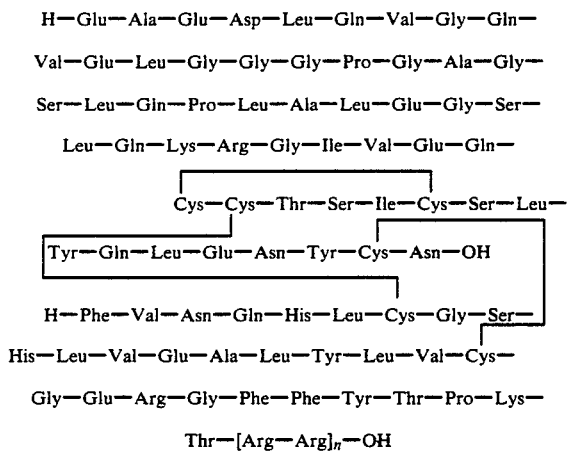

His—Leu—Val—Glu—Ala—Leu—Tyr—Leu—Val—Cys—

Gly—Glu—Arg—Gly—Phe—Phe—Tyr—Thr—Pro—Lys—

Thr—[Arg—Arg]$_n$—OH and pharmaceutically acceptable non-toxic salts thereof in which n is zero or one.

DETAILED DESCRIPTION OF THE INVENTION

This invention is directed to two peptides, either of which may be in the form of its pharmaceutically acceptable non-toxic salt.

The peptide sequences and corresponding short-hand descriptions used herein in which the term HPI denotes human proinsulin are as follows:

H—Glu—Ala—Glu—Asp—Leu—Gln—Val—Gly—Gln—

Val—Glu—Leu—Gly—Gly—Gly—Pro—Gly—Ala—Gly—

Ser—Leu—Gln—Pro—Leu—Ala—Leu—Glu—Gly—Ser—

Leu—Gln—Lys—Arg—Gly—Ile—Val—Glu—Gln—

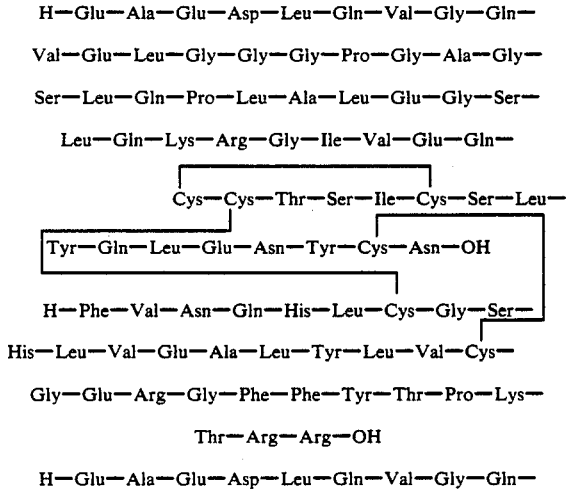

His—Leu—Val—Glu—Ala—Leu—Tyr—Leu—Val—Cys—

Gly—Glu—Arg—Gly—Phe—Phe—Tyr—Thr—Pro—Lys—

Thr—Arg—Arg—OH

H—Glu—Ala—Glu—Asp—Leu—Gln—Val—Gly—Gln—

Val—Glu—Leu—Gly—Gly—Gly—Pro—Gly—Ala—Gly—

Ser—Leu—Gln—Pro—Leu—Ala—Leu—Glu—Gly—Ser—

Leu—Gln—Lys—Arg—Gly—Ile—Val—Glu—Gln—

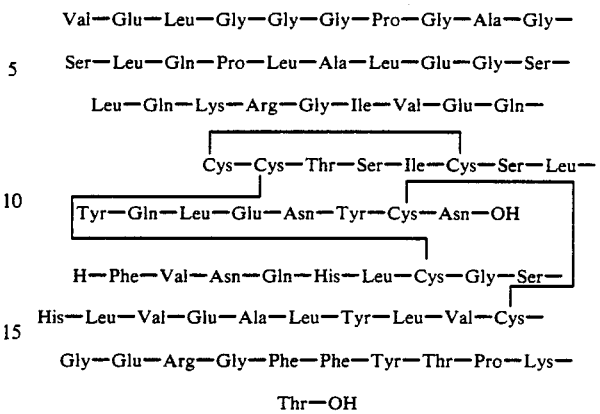

His—Leu—Val—Glu—Ala—Leu—Tyr—Leu—Val—Cys—

Gly—Glu—Arg—Gly—Phe—Phe—Tyr—Thr—Pro—Lys—

Thr—OH

Included in the compounds of this invention are their pharmaceutically acceptable non-toxic acid addition salts and their pharmaceutically acceptable non-toxic carboxylic acid salts.

The term "pharmaceutically acceptable non-toxic acid addition salts" encompasses both organic and inorganic acid addition salts including, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or salts, such as, for example, ammonium bicarbonate. Preferably, the acid addition salts are those prepared from hydrochloric acid, acetic acid, or carbonic acid. Any of the above salts can be prepared by conventional methods.

The term "carboxylic acid salts" includes, for example, zinc, ammonium, alkali metal salts such as sodium, potassium, and lithium, and the like. Preferred carboxylic acid salts are the zinc and sodium salts.

For the sake of convenience, the amino acids of the peptides referred to herein may be described by their approved single-letter or three-letter shorthand designations.

| Single-Letter | Three-Letter | Amino Acid |
|---|---|---|
| A | Ala | Alanine |
| R | Arg | Arginine |
| N | Asn | Asparagine |
| D | Asp | Aspartic Acid |
| C | Cys | Cysteine |
| E | Glu | Glutamic Acid |
| Q | Gln | Glutamine |
| G | Gly | Glycine |
| H | His | Histidine |
| I | Ile | Isoleucine |
| L | Leu | Leucine |
| K | Lys | Lysine |
| F | Phe | Phenylalanine |
| P | Pro | Proline |
| S | Ser | Serine |
| T | Thr | Threonine |
| Y | Tyr | Tyrosine |
| V | Val | Valine |

The compounds of this invention can be prepared by routine peptide synthesis methods.

Alternatively, and preferably, the compounds of this invention can be prepared from human proinsulin. Human proinsulin is available via a variety of routes, including organic synthesis, isolation from human pancreas by conventional methodology, and, more recently, recombinant DNA methodology.

In broad outline, the production of proinsulin using recombinant DNA methodology involves obtaining, whether by isolation, construction, or a combination of both, a sequence of DNA coding for the amino acid sequence of human proinsulin. The DNA coding for human proinsulin then is inserted in reading phase into a suitable cloning and expression vehicle. The vehicle is used to transform a suitable microorganism after which the transformed microorganism is subjected to fermentation conditions leading to (a) the production of additional copies of the human proinsulin gene-containing vector and (b) the expression of human proinsulin or a human proinsulin precursor product.

In the event the expression product is a human proinsulin precursor, it generally will comprise the human proinsulin amino acid sequence joined at its amino terminal to another protein, whether foreign or that normally expressed by the gene sequence into which the human proinsulin gene has been inserted. The human proinsulin amino acid sequence is joined to the protein fragment through a specifically cleavable site, typically methionine. This product is customarily referred to as a fused gene product.

The human proinsulin amino acid sequence is cleaved from the fused gene product using cyanogen bromide after which the cysteine sulfhydryl moieties of the human proinsulin amino acid sequence are stabilized by conversion to their corresponding S-sulfonates.

The resulting human proinsulin S-sulfonate is purified, and the purified human proinsulin S-sulfonate then is converted to human proinsulin by formation of the three properly located disulfide bonds, using, for example, the method of U.S. Pat. No. 4,430,266. The resulting human proinsulin product then is purified using recognized methodology.

The compounds of this invention can be prepared by enzymatic digestion of human proinsulin. Thus, treatment of human proinsulin with trypsin leads to the production of, among others, (32-33 split)HPI. Treatment of the product mixture by gel filtration followed by reverse phase high performance liquid chromatography (HPLC) permits recovery of purified (32-33 split)HPI.

The (32-33 split)HPI is used to prepare the other compound of this invention. Thus, treatment of (32-33 split)HPI with carboxypeptidase B yields des(31,32)HPI.

As noted, the compounds of this invention have an insulin-like, anti-diabetic effect substantially greater than that recognized for human proinsulin.

The compounds of this invention, due to their insulin-like activity, are useful in the treatment of diabetes. As such, they can be used in a variety of pharmaceutical compositions and formulations and can be administered by a variety of conventional routes, such as intramuscular, intravenous, subcutaneous, and intraperitoneal.

In administering the compounds of this invention, the pharmaceutical forms suitable for injection include sterile aqueous solutions or dispersions and sterile powders for reconstitution into sterile injectable solutions or dispersions.

Sterile injectable solutions can be prepared by incorporating the compounds of this invention in the calculated amount of the appropriate solvent along with various of the other ingredients, as desired.

The following examples are provided to illustrate this invention. They are not intended to be limiting on the scope thereof.

EXAMPLE 1

Preparation of (32-33 split)HPI

Human proinsulin (312 mg wet wt.) was dissolved in 57 ml of 0.1M Tris buffer (final pH 7.0), and the solution was warmed to 25° C. in a water bath. Trypsin (25.1 micrograms) dissolved in 57 microliters of 0.05M Tris-0.02M $CaCl_2$ (pH 7.0) was added. The reaction was terminated after 68 minutes by lowering the pH of the solution to 2.5 by addition of acetic acid.

The acidified solution (57 ml) was chromatographed on a 5×200 cm G50 Superfine Sephadex column at 6° C. using 1M molar acetic acid as the column solvent. A large broad peak containing unreacted HPI, (32-33 split)HPI, and (65-A1 split)HPI eluted first and was fairly well separated from a second peak containing di-$Arg^{31,32}$ human insulin.

Column fractions were pooled as follows:

| Pool | Beginning and end points of pool | Protein content of pool as determined by u.v.* |
|---|---|---|
| A | 1768-2146 ml | 83.3 mg of a mixture of HPI and monosplit HPI's |
| B | 2146 ml-2464 ml | 98.1 mg of a mixture of HPI and monosplit HPI's |
| C | 2464 ml-2843 ml | 34 mg of di-$Arg^{31, 32}$ human insulin |

*Amounts calculated based on $O.D.^{276}$ and a calculated extinction coefficient.

The above pools were lyophilized.

The components in the three lyophilized pools were further resolved by chromatographing the materials in three portions on a 2.5×60 cm C-18 HPLC column using 34% $CH_3CN$ in 0.5% trifluoroacetic acid as the column solvent.

A portion (79 mg) of Pool A dissolved in dilute HCl (final pH=2) was applied to the column and yielded two pools of interest (D and E).

| Pool | Beginning and end points of pool | Protein content of pool as determined by u.v. |
|---|---|---|
| D | 519-627 ml | 34.4 mg of pure (32-33 split) HPI [43% of 79 mg] |
| E | 700-808 ml | 14.7 mg of 70% pure (65-A1 split) HPI [18.5% of 79 mg] |

Pool D was lyophilized to obtain pure (32-33 split)HPI. The purity of the sample was determined using analytical HPLC, polyacrylamide basic disc gel electrophoresis, and analytical Fast Protein Liquid Chromatography (FPLC). Amino acid analysis and amino acid sequencing were used to establish the identity of the compound.

EXAMPLE 2

Preparation of des(31,32)HPI (32-33 split)HPI (27.93 mg wet wt.) dissolved in 5.0 ml of 0.1M Tris (final pH 7.0) was treated with 39.4 μg of Carboxypeptidase B for 32 minutes at 25° C. The reaction was terminated by acidifying the mixture to pH 2.7 with 1M HCl. The resulting solution was chromatographed on a 0.9×40 cm G25 M Sephadex column packed in 2% acetic acid to obtain 16.6 mg (u.v. wt.) of protein.

The protein (14.59 mg wet wt.) was chromatographed at 6° C. on a 2.5×125 cm G50 SF Sephadex column packed in 1M acetic acid to obtain 11.1 mg (u.v. wt.) of protein.

Final protein purification was achieved using a 5×50 mm Pharmacia Mono S cation exchange column. The initial and final column solvents were:
Initial—7M urea—0.1M acetic acid
Final—7M urea—0.1M acetic acid—1M NaCl A linear gradient from 0 to 0.3M NaCl over a 30 minute period was used to elute the protein. The main peak material was chromatographed on a 0.9×40 cm G25 M Sephadex column packed in 2% acetic acid to obtain 6.22 mg (u.v. wt.) of highly pure des(31,32)HPI.

Biological Activity

A. IM-9 Radioreceptor Assay

IM-9 cells were grown in RPMI media containing 2 mM glutamine, 25 mM HEPES, and 10% fetal bovine serum. Cells were harvested by centrifugation, washed, and resuspended in HEPES assay buffer, pH 7.6 [De-Meyts, P., Insulin and Growth Hormone Receptors in Human Cultured Lymphocytes and Peripheral Monocytes, Blecher, M., Ed., New York, Marcel Dekker, Inc, 301-330 (1976)]. Cell viability, determined by exclusion of trypan blue, was greater than 90% in each experiment. Triplicate tubes were prepared, each set containing 100 $\mu$l of assay buffer, human insulin, human proinsulin, or a compound of this invention, 200 $\mu$l $^{125}$I-insulin (final concentration 1-2×10$^{-11}$M), and 200 $\mu$l cells (about 500,000 cells). Incubations were carried out in 1.5 ml microfuge tubes at 15° C. for two hours. Concentrations of stock solutions containing insulin, proinsulin, or compound of this invention used in the binding studies were established by amino acid analysis and by their absorbance at 276 nm. The cells were resuspended during the assay every 30 minutes by inverting the tubes several times. At the end of the incubation, the tubes were centrifuged for one minute in a Beckman Microfuge, the supernant was aspirated, the tips of the tubes containing the cell pellet were excised, and the radioactivity was measured.

The results from the foregoing are provided in Table I following.

TABLE I

| IM-9 Radioreceptor Assay | | |
|---|---|---|
| Compound | ED$_{50}$ (M) | Relative Potency |
| Human Insulin | 4.27 ± 0.3 × 10$^{-10}$ | 70 |
| Human Proinsulin | 2.97 ± 0.2 × 10$^{-8}$ | 1 |
| (32-33 split) HPI | 5.92 ± 0.7 × 10$^{-9}$ | 5 |
| des (31,32) HPI | 5.60 ± 0.3 × 10$^{-9}$ | 5 |

B. Isolated Fat Cell Radioreceptor Assay

Isolated fat cells were prepared by a modification [Huber, C. T., Solomon, S. S., and Duckworth, W. C., J. Clin. Invest. 65, 461-468 (1980)] of the method described in Rodbell, M., J. Biol. Chem. 239, 375-380 (1964). All incubations were in Krebs-Ringer-Hepes (KRH) buffer, pH 7.4, with 4% bovine serum albumin (BSA) in a total volume of 2 ml. The fat cells were incubated at 15° C. for two hours with $^{125}$I-labeled insulin (1-2×10$^{-11}$M) and, at a selected concentration, with buffer or human insulin or human proinsulin or a compound of this invention. At selected times, triplicate 300 $\mu$l aliquots were removed and added to microfuge tubes containing 100 $\mu$l dinonyl phthalate [see Gliemann, J., Osterlind, K., Vinten, J., and Gammeltoft, S., Biochem. Biophys. Acta. 286, 1-9 (1972)]. After centrifugation for one minute in a microfuge, the tubes were cut through the oil layer, and the cell pellet was counted using a gamma counter to determine binding. Degradation of the $^{125}$I-labeled insulin was determined by adding the buffer layer from the microfuge tube to ice-cold KRH buffer followed immediately by sufficient trichloroacetic acid to give a final concentration of 5%.

The results from the foregoing are provided in Table II following.

TABLE II

| Isolated Fat Cell Radioreceptor Assay | | |
|---|---|---|
| Compound | ED$_{50}$ (M) | Relative Potency |
| Human Insulin | 1.43 ± 0.2 × 10$^{-9}$ | 178 |
| Human Proinsulin | 2.55 ± 0.6 × 10$^{-7}$ | 1 |
| (32-33 split) HPI | 5.29 ± 1.8 × 10$^{-8}$ | 5 |
| des (31,32) HPI | 2.85 ± 0.1 × 10$^{-8}$ | 9 |

C. Biological Activity in Isolated Rat Adipocytes

Adipocytes were prepared from epididymal fat pads by a modification (Huber, supra) of the collagenase digestion procedure of Rodbell, supra. Krebs-Ringer-HEPES (KRH) buffer, pH 7.4, containing 4% bovine serum albumin and 0.55 mM glucose was used in all isolation and incubation steps.

Approximately 2×10$^5$ adipocytes were incubated in one ml of buffer with $^{125}$I-(A14) pork insulin and varying concentrations of unlabeled human insulin, human proinsulin, or a compound of this invention. Incubations were conducted at 15° C. for 4.5 hrs. At the end of the incubation period, triplicate samples were withdrawn for determination of binding (cell-associated radioactivity) as described in Frank, B. H., Peavy, D. E., Hooker, C. S., and Duckworth, W. C., Diabetes 32, 705-711 (1983). At the 15° C. temperature of the incubation, no degradation of the tracer insulin was detectable. Samples were counted with a Tracor Analytic Model 1285 gamma scintillation spectrometer with a counting efficiency of 85%.

Biological activity was assessed according to the method of Moody, A. J., Stan, M. A., Stan, M., and Glieman, J., Horm. Metab. Res. 6, 12-16 (1974) by monitoring the incorporation of 2-$^3$H-glucose in total fat cell lipid. Cells were incubated with varying concentrations of cold human insulin, human proinsulin, or a compound of this invention at 37° for 1 hr, and the reaction then was terminated by the addition of 10 ml of Liquifluor (New England Nuclear). Radioactivity was determined in a Searle Isocap 300 liquid scintillation counter at an efficiency of approximately 30%. Blanks were prepared in which the scintillation fluid was added to the vials prior to the addition of cells. The average counts obtained from these vials were subtracted from those observed in all other samples.

Competitive binding curves and biological activity dose-response curves were analyzed using the PREFIT and ALLFIT programs [DeLean, A., Munson, P. J., and Rodbard, D., Am. J. Physiol. 235, E97-E102 (1978)] based on a four-parameter logistic model. These analyses indicated the concentration of insulin or proinsulin necessary to produce a half-maximal response, as well as the maximal and minimal values. All values are presented as the mean ±SEM.

The results from the foregoing are provided in Table III following.

TABLE III
Biological Activity in Isolated Rat Adipocytes

| Compound | $ED_{50}$ (M) | Relative Potency |
|---|---|---|
| Human Insulin | $5.32 \pm 0.7 \times 10^{-11}$ | 233 |
| Human Proinsulin | $1.24 \pm 0.2 \times 10^{-8}$ | 1 |
| (32–33 split) HPI | $2.56 \pm 0.2 \times 10^{-9}$ | 5 |
| des (31,32) HPI | $2.68 \pm 0.5 \times 10^{-9}$ | 5 |

We claim:

1. A compound of the formula

H—Glu—Ala—Glu—Asp—Leu—Gln—Val—Gly—Gln—

Val—Glu—Leu—Gly—Gly—Gly—Pro—Gly—Ala—Gly—

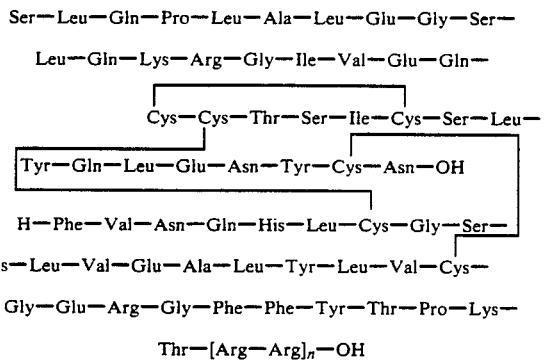

or a pharmaceutically acceptable salt thereof in which n is zero or one.

2. Compound of claim 1, in which n is zero.
3. Compound of claim 1, in which n is one.

* * * * *